United States Patent [19]

Moesgaard

[11] Patent Number: 5,919,820
[45] Date of Patent: Jul. 6, 1999

[54] ANTIOXIDANT MEDICAMENT

[75] Inventor: Sven Moesgaard, Almind, Denmark

[73] Assignee: Pharma Nord ApS, Vojens, Denmark

[21] Appl. No.: 08/850,723

[22] Filed: May 2, 1997

[30] Foreign Application Priority Data

May 2, 1996 [GB] United Kingdom .................... 9609218

[51] Int. Cl.⁶ .................................................. A61K 31/375
[52] U.S. Cl. ............................................. 514/474; 514/492
[58] Field of Search ...................................... 514/474, 492

[56] References Cited

U.S. PATENT DOCUMENTS 4,927,850  5/1990  Bayless et al. .

FOREIGN PATENT DOCUMENTS

| | | |
|---|---|---|
| 0 345 247 | 12/1989 | European Pat. Off. . |
| 0 351 856 | 1/1990 | European Pat. Off. . |
| 0 511 895 | 11/1992 | European Pat. Off. . |
| 0 519 876 | 12/1992 | European Pat. Off. . |
| 0 542 632 | 5/1993 | European Pat. Off. . |
| 0 579 958 | 1/1994 | European Pat. Off. . |
| 0 655 460 | 5/1995 | European Pat. Off. . |
| 0 705 542 | 4/1996 | European Pat. Off. . |
| 2 100 669 | 3/1972 | France . |
| 2 336 176 | 1/1974 | Germany . |
| 35 42 309 | 6/1987 | Germany . |
| 37 22 647 | 1/1989 | Germany . |
| 43 38 314 | 3/1995 | Germany . |
| 1 444 024 | 7/1976 | United Kingdom . |
| WO 90/07928 | 7/1990 | WIPO . |
| WO 91/09524 | 7/1991 | WIPO . |
| WO 91/11117 | 8/1991 | WIPO . |
| WO 95/33486 | 12/1995 | WIPO . |

OTHER PUBLICATIONS

"Nature's Best Health for Life Catalogue", 1995/96, p. 37, 42 and 64.

*Primary Examiner*—James H. Reamer
*Attorney, Agent, or Firm*—Oblon, Spivak, McClelland, Maier & Neustadt, P.C.

[57] ABSTRACT

Antioxidative pharmaceutical formulation comprising L-selenomethionine, β-carotene, ascorbic acid (vitamin C), D-α-tocopherylacetate (vitamin E) and L-methionine together with a pharmaceutically acceptable carrier therefor.

4 Claims, No Drawings

ANTIOXIDANT MEDICAMENT

TECHNICAL FIELD

The present invention relates to an antioxidative pharmaceutical formulation suitable for use in the treatment of diseases caused by oxidative stress, in particular pancreatitis. The invention also relates to the use of particular vitamins, amino acids and trace elements for the preparation of a medicament suitable for the treatment of oxidative stress.

BACKGROUND ART

Oxidative stress is the term used to describe a biological state where the production of harmful oxidants by bodily systems or extern sources overwhelms the natural antioxidant defences leading to cellular and tissue damage or destruction. These oxidants may be free radicals or reactive oxygen species, both may be rendered inactive by the natural antioxidant defence systems of the body. Oxidative stress has been implicated as a contributory factor in many diseases, for example atherosclerosis and its consequences, respiratory diseases, arthritis, cancer, diseases of the nervous system, e.g. Parkinson's disease, and of the digestive system, e.g. pancreatitis. Under certain conditions the activity of the immune system may be impaired. Naturally occurring antioxidants include some vitamins e.g. vitamins C and E; some phytochemicals e.g. flavonoids; certain inorganic elements e.g. selenium. These may be incorporated into enzymes that scavenge the oxidant species and render them harmless. These enzymes may be metalloproteins that incorporate trace elements such as selenium. A typical example is the selenium containing enzyme glutathione peroxidase. Deficiencies in the diet of the amino acid precursors used in the biosynthesis of these enzymes and the essential trace elements or their poor bio-availability, can result in impairment of protective enzymes leading to the signs of oxidative stress.

Acute, recurrent and chronic pancreatitis are common disorders affecting 1 in 20,000 of the adult population of the developed nations, the prevalence in the under developed countries is believed to be higher. The pathogenesis of the forms of pancreatitis is the subject of debate, but chemical insults from xenobiotics and viral infection are implicated in many cases. Both also can cause an increase in free radical production, and it is possible that it is this effect that initiates and perpetuates pancreatitis.

The standard treatment for recalcitrant chronic pancreatitis is a partial pancreatectomy, the cost of which is about £12,000. Manchester Royal Infirmary normally perform about 72 such operations per annum. With extrapolation to 20 centres in the whole country, the cost to the National Health Service of this form of treatment is in the region of £17¼million per year.

Patients with acute and chronic pancreatitis have been shown to have dietary intakes of antioxidants (Rose et. al. *Hum. Nutr. Clin. Nutr.;* 40(2); 151–64; 1986), blood levels of ascorbic acid, selenium, β-carotene, vitamin E (Uden et al. *Aliment. Pharmacol. Ther.;* 6(2); 229–40; 1992) and glutathione that are below normal levels.

Treatment with antioxidant therapy and methionine has resulted in patients showing clinical improvement as demonstrated by a reduction in the degree and severity of symptoms associated with a restoration to normal of the sub-optimal levels of blood micro-nutrients. (Braganza et al. Pancreas; 2(4); 489–94; 1987).

Xenobiotic induced pancreatitis can also be managed with antioxidants (Uden et al. *Aliment. Pharmacol. Ther.;* 4(4); 357–71; 1990).

In these studies, however, a combination of different product formulations have been used. These have proved unsatisfactory in practice as the poor bioavailability of the selenium has necessitated the use of multiple tablet mixes of up to 24 tablets per day. This is clinically undesirable as many patients with pancreatitis have a disordered digestive system and dysphagia and find it difficult to comply with the dosage regime. Furthermore, as pancreatitis is often accompanied by impaired absorption of nutrients, the bioavailability of the micro-nutrients can be a limiting factor in any attempts to restore their levels to the optimum.

An antioxidative pharmaceutical formulation has now been prepared, which comprises antioxidative micronutrients suitable for alleviating the symptoms of pancreatitis, together with methionine, and which removes the requirement to take large numbers of tablets daily. The novel formulation presents the micro-nutrients in a highly bioavailable and safe form.

BRIEF DESCRIPTION OF THE INVENTION

According to the invention there is provided an antioxidative pharmaceutical formulation comprising L-selenomethionine, β-carotene, ascorbic acid (vitamin C), D-α-tocopherylacetate (vitamin E) and L-methionine together with a pharmaceutically acceptable carrier therefor.

Preferably the pharmaceutical formulation comprises from 60 to 90 μg selenium (from L-selenomethionine), from 2.4 to 3.6 mg β-carotene, from 120 to 180 mg ascorbic acid, from 38 to 56 mg vitamin E and from 320–480 mg of L-methionine, together with a suitable carrier.

According to a second aspect of the invention there is provided the use of L-methionine for the preparation of a medicament for the treatment of diseases caused by oxidative stress. Diseases that are thought to be caused by oxidative stress include pancreatitis, hepatic disorders such as primary biliary cirrhosis, hepatitis C and intra-hepatic cholestasis, as well as Parkinson's disease and Alzheimer's disease. In addition to the use of L-methionine for the preparation of a suitable medicament, L-selenomethionine, β-carotene, ascorbic acid, and/or vitamin E may also be used in the preparation.

The medicament of this invention may be formulated for oral administration and therefore may be presented as plain or coated tablets, soft capsules made for example from gelatin or vegetable gel, or as a sustained release formulation. Alternatively, the formulation may be in liquid form suitable for administration by ingestion, such as a syrup or elixir, or by intra-gastric administration.

In yet further alternative formulations the combination of vitamins, trace elements and sulphur-containing amino acids may be prepared as a suppository for rectal administration. For intravenous, intramuscular or subcutaneous administration a suitable liquid formulation can be prepared.

Excipients which may be incorporated with the active ingredients include carriers, binders, stabilizers, preservatives and flavours. Examples of suitable excipients which may be incorporated into the formulations include a binder such as gum tragacanth, acacia, corn starch, or gelatin; an excipient such as microcrystalline cellulose; a disintegrating agent such as corn starch, pregelatinized starch, alginic acid and the like; a lubricant such as stearic acid or magnesium stearate; a sweetening agent such as sucrose, lactose or saccharin, a flavouring agent such as orange, peppermint, oil of wintergreen or cherry. When the formulation is a capsule, it may contain, in addition to materials of the above type, a liquid carrier such as fatty oil. Various other materials may be present as coatings or to otherwise modify the physical form of the formulation. For instance, tablets may be coated with shellac, sugar or both. A syrup or elixir may contain the active compound, sucrose as a sweetening agent, methyl and propyl parabens as preservatives, a dye and a flavouring such as cherry or orange flavour.

The formulation, according to the invention may be administered by mouth, injection or intravenous infusion from one to four times daily, preferably three or four times daily.

One advantage of the formulation of the present invention is that a patient suffering from pancreatitis need only take a single tablet four times a day, a dosage regime which is easy to comply with. The cost per patient of such treatment is in the region of £200 per annum, which would result in a saving to the National Health service of £15 million per annum.

According to yet a further aspect of the invention there is provided a method of treating diseases resulting in whole or in part from oxidative stress, for example acute, chronic or recurrent pancreatitis, hepatic disorders such as primary biliary cirrhosis, hepatitis C and intra-hepatic cholestasis, myocardial infarction, Parkinson's disease and Alzheimer's disease, which comprises administering to a patient in need of such treatment a pharmaceutical formulation comprising L-selenomethionine, β-carotene, ascorbic acid, D-α-tocopherylacetate and L-methionine together with a pharmaceutically acceptable carrier therefor.

The invention will be further described by way of reference to the following example.

EXAMPLE 1

A pharmaceutical formulation was prepared in tablet form using standard compression techniques. Each tablet had the following composition:

| | |
|---|---|
| Selenium (from L-selenomethionine) | 75 μg |
| β-carotene | 3 mg |
| Ascorbic acid | 150 mg |
| Vitamin E | 47 mg |
| L-methionine | 400 mg |

In addition each tablet contained the following inactive ingredients:

| | |
|---|---|
| Microcrystalline cellulose | 134 mg |
| CrossCarmellose Sodium | 30 mg |
| Silica | 12 mg |
| Magnesium stearate | 6 mg |

Each tablet was coated with a film coating having the following composition:

| | |
|---|---|
| Hydroxypropylmethyl cellulose | 16.7 mg |
| Riboflavin (as colouring) | 10.6 mg |
| Talc | 7.1 mg |
| Titanium dioxide | 3.6 mg |
| Corn protein | 2.0 mg |

During the coating process water is used as a solvent and dispersing agent. The coating is coloured to aid identification, to protect the components from degradation and to improve swallowing characteristics.

The resultant film coated tablets were yellow, oval, 16×19 mm with convex sides with an average weight of 970 mg.

What is claimed as new and desired to be secured by Letters Patent of the United States is:

1. A composition comprising:

60–90μ selenium;

2.4–3.6 mg β carotene;

120–180 mg ascorbic acid;

38 to 56 mg D-α-tocopherylacetate;

320 to 480 mg L-methionine; and a pharmaceutically acceptable carrier in unit dosage form.

2. The composition of claim 1, wherein the selenium is complexed as L-selenomethionine.

3. A method of treating acute, chronic or recurrent acute pancreatitis comprising administering to a patient in need thereof a composition comprising:

60–90μ selenium;

2.4–3.6 mg β carotene;

120–180 mg ascorbic acid;

38 to 56 mg D-α-tocopherylacetate;

320 to 480 mg L-methionine; and a pharmaceutically acceptable carrier.

4. The method of claim 3, wherein the selenium is complexed as L-selenomethionine.

* * * * *